US005674055A

United States Patent [19]
Nimberger et al.

[11] Patent Number: 5,674,055
[45] Date of Patent: Oct. 7, 1997

[54] PISTON SEALING ARRANGEMENT FOR A SAMPLING PUMP SYSTEM

[75] Inventors: Spencer M. Nimberger, Houston; Robert L. Ward, Missouri City, both of Tex.

[73] Assignee: PGI International, Ltd., Houston, Tex.

[21] Appl. No.: 583,558

[22] Filed: Jan. 5, 1996

Related U.S. Application Data

[62] Division of Ser. No. 243,844, May 16, 1994, Pat. No. 5,498,138.

[51] Int. Cl.⁶ .................................................. F04B 53/02
[52] U.S. Cl. ........................... 417/313; 417/440; 277/165
[58] Field of Search ............................... 417/313, 440, 417/401; 92/193; 277/165

[56] References Cited

U.S. PATENT DOCUMENTS

| | | |
|---|---|---|
| 1,199,526 | 9/1916 | Bowser . |
| 3,156,160 | 11/1964 | Meyer et al. . |
| 4,093,406 | 6/1978 | Miller . |
| 4,276,001 | 6/1981 | Holmes .................................. 417/401 |
| 4,531,895 | 7/1985 | Zeck . |
| 4,565,504 | 1/1986 | George et al. . |
| 4,628,750 | 12/1986 | Welker . |
| 4,714,259 | 12/1987 | Mack et al. ............................. 277/165 |
| 4,928,536 | 5/1990 | Welker ................................... 73/863.83 |
| 5,000,077 | 3/1991 | Habicht . |
| 5,032,063 | 7/1991 | Zeck et al. . |
| 5,074,154 | 12/1991 | Allen et al. ............................. 417/553 |
| 5,090,438 | 2/1992 | Nimberger . |
| 5,092,742 | 3/1992 | Allen et al. ............................. 417/313 |
| 5,152,678 | 10/1992 | Zeck . |
| 5,159,814 | 11/1992 | Jakobsson ............................... 277/165 |
| 5,191,801 | 3/1993 | Allen et al. . |
| 5,213,586 | 5/1993 | Welker . |
| 5,472,216 | 12/1995 | Albertson et al. ....................... 277/165 |

*Primary Examiner*—Timothy Thorpe
*Assistant Examiner*—Roland G. McAndrews, Jr.
*Attorney, Agent, or Firm*—Browning Bushman

[57] ABSTRACT

An improved sampling pump has utility for withdrawing fluid from a pressurized source and outputting fluid to a sampling container. The fluid pump assembly of the present invention includes an operator unit for reciprocating a plunger, and a side body port positioned within the pump body for receiving a removable filter. A pressure regulator has an inlet positioned within a side body port of the pump body and regulator outlet port in fluid communication with the operator unit. A collar rotatable with respect to a regulator housing is provided for reducing installation costs and for optionally removing condensate from the regulator. An adjustable discharge valve is pressure balanced for increasing the reliability of the pump. An improved seal is utilized for dynamic seal engagement between the pump body and the pump plunger.

18 Claims, 4 Drawing Sheets

PISTON SEALING ARRANGEMENT FOR A SAMPLING PUMP SYSTEM

RELATED CASE

This is a Division of Application Ser. No. 08/243,844, filed May 16, 1994, now U.S. Pat. No. 5,498,138.

FIELD OF THE INVENTION

The present invention relates to pumps which periodically withdraw fluid from a source and pass the fluid to a downstream container or other device. More particularly, the present invention relates to a pump ideally suited for periodically withdrawing gas from a relatively high pressure line, then outputting the gas to a sampling container. The pump operator may be powered by the source, and pressure to the operator may be controlled by a regulator.

BACKGROUND OF THE INVENTION

Various situations arise wherein one seeks to pump a liquid or gas frost a pressurized source, such as a flow line, and output the fluid to a downstream container, such as a sample bottle. The sample bottle may, for example, be periodically sent to a laboratory for analysis to determine the BTU content of the sampled fluid, and thereby determine the BTU content of the gas flowing in the pressurized line. In many situations, a separate power source, such as an electric pump or pressurized hydraulic line, is readily available for driving the pump. In other situations typified by remote applications, a separate power source is not readily available or is not cost-effective for driving or powering the pump. In these latter situations, the pressured source can be used to drive the pump, thereby avoiding the expenses associated with a separate power supply. Prior art sampling pumps have; been powered by an operator unit which receives pressure from the pressurized source, and which uses the pressure as the driving force. Examples of sampling pumps which may utilize the pressurized line as the driving force for the pump operator are disclosed in U.S. Pat. Nos. 4,928,536 and 5,032,063.

Many of the advantages of a sampling pump powered by a fluid pressure source frequently are not realized if the fluid is contaminated with particles, such as rust, scale, or other particulate. The fluid ideally is filtered before entering the pump to reduce maintenance costs, and this filter ideally is closely adjacent the pump inlet port check valve. If the fluid line to the pump operator unit is not also filtered, however, service costs for the operator unit can become excessive. Service personnel periodically change the pump inlet filter, and may not inspect or change the pump operator filter.

In some applications, the pump inlet filter may be cleaned by the fluid itself, as disclosed in U.S. Pat. No. 5,074,154. Much of the fluid flowing to a sampling pump may thus pass by, rather than through, the pump inlet filter in a "hot loop", thereby continually cleaning the pump inlet filter. In other applications, this hot loop technique is not feasible, and substantially all fluid flow to the pump is input and discharged from the pump.

In many applications, a check valve is provided within the flow line downstream from the sampling pump. When used for gas applications, the pump discharge check valve ideally is closely adjacent the pump plunger, thereby minimizing the "dead areas" within the pumping system and improving pump efficiency, as disclosed in U.S. Pat. No. 5,074,154.

U.S. Pat. No. 5,191,801 discloses an improved fluid sampling pump including a line pressure driven actuator for pumping low pressure fluid to a sample container. The pump disclosed in this patent is not designed for pumping line fluid under a high pressure, e.g., 500 psi. Moreover, if line pressure increases considerably by, for example, 200 psi, the higher pressure fluid could pass through the pump to unintentionally fill the sample container. While line pressure to the actuator conceptually may be reduced, various practical problems are encountered when placing a pressure regulator between the pump bore and the actuator. A regulator of the type disclosed in U.S. Pat. No. 5,098,438 cannot be easily supported structurally by the pump body. Water in the fluid line may condense in the pressure regulator, thereby adversely affecting the operation of the regulator and/or the downstream pump actuator. Another problem with prior art sampling pumps relates to the life of the pump piston seal, particularly when the pump is being used for pumping various types of fluids normally deleterious to conventional O-ring materials.

The disadvantages of the prior art are overcome by the present invention, and a novel pump is hereinafter disclosed to satisfy the need for a reliable pump which may be used for various applications.

SUMMARY OF THE INVENTION

The sampling pump of the present invention, in a preferred embodiment, utilizes a pump operator unit comprising an operator piston responsive to upstream fluid pressure to drive the operator and therefore stroke the pump plunger, so that a separate pump power source is not required to perform this function.

The pump includes a filter positioned in a side body port of the pump body by a removable plug, so that the plug and filter may be periodically removed, the filter cleaned, and the filter and plug reinstalled without disassembling the pump from the upstream source or the downstream container, e.g., sample bottle. The filter is provided between the pump body inlet and the pump inlet check valve, and an actuation line to the pump actuator has its actuator line inlet hydraulically spaced between the filter and the pump inlet check valve. All fluids passing to either the pumping chamber or to the pump operator are thus filtered to enhance the life of the pump assembly.

The pump outlet check valve engages a seat within the body of the pump, so that dead areas within the pump are minimized. The check valve is balanced, as explained subsequently, so that its operation is not dependent upon a constant line pressure. A purge line is provided within the pump body for interconnecting the pump inlet port and the pump outlet port, and fluid flow through this line may be controlled by a purge valve member having its seat also within the pump body. The purge valve is ideally positioned opposite the pump outlet check valve with respect to the central axis of the pump, and the pump body outlet port is positioned circumferentially between the purge valve and the check valve. An actuator line port is also positioned circumferentially between the purge valve and the check valve, but is opposite the pump body outlet port with respect to the pump centerline.

According to one embodiment of the invention, a regulator has its inlet within the actuator line port of the pump body, and is secured directly to the body of the pump, so that the pump bore for receiving the piston is substantially adjoining the inlet port to the regulator body. The regulator is provided with a collar rotatable to a selected position with respect to the regulator body, so that a fluid communication port through the collar may be rotated to a selected position with respect to the regulator body for hard piping the output from the regulator to the pump actuator. Various techniques are disclosed for removing water from the regulator, so that condensation within the regulator does not affect the operation of the regulator. By removing the condensation before the fluid is passed to the pump actuator, the life of the actuator is also increased. In one embodiment, a plurality of circumferentially spaced water discharge ports are provided about a nut threaded to the regulator body. The nut may be partially unthreaded during service of the actuator pump, so that line pressure blows the accumulated condensate out the lower one of the discharge ports through the nut.

A balanced check valve is provided for controlling the flow from the pump to the downstream container. The balanced check valve is responsive to fluctuations in the line pressure, so that fluid is only pumped from the line to the sample container when intended. When line pressure is below a selected value, a spring biased check valve, only passes fluid to the operator under a high pressure generated by the pumping stroke. When line pressure is above the selected value, the check valve becomes balanced to prevent the higher pressure fluid from passing directly to the downstream container.

The fluid sampling pump may also be provided with an improved piston seal for dynamic sealing engagement with the sidewalls of the pump body bore. A polytetrafluoroethylene seal component is provided for dynamic sealing engagement with the sidewalls of the bore, while an elastomeric seal component provides a static seal between the piston and the polytetrafluoroethylene component, and also continually biases the polytetrafluoroethylene component into reliable sealing engagement with the sidewalls of the pump body bore.

It is an object of the present invention to provide an improved sampling pump with a filter which may be replaced without disassembling the pump from either its upstream or downstream lines.

Another object of the present invention is a sampling pump with a balanced pump outlet check valve to control downstream pressure, with the check valve inlet being positioned within the pump body to minimize dead volumes within the pump.

Yet another object of this invention is to provide a sampling pump with an output check valve and purge valve positioned on opposite sides of the pump centerline, and each of an output port and actuator line port being circumferentially positioned between these valves and opposite each other.

It is another object of the invention to provide a sampling pump which is capable of reliably pumping both relatively high pressure fluids and relatively low pressure fluids from a source to a sample container.

Yet another object of this invention is to improve the reliability and life of the pump by providing an improved seal for dynamic sealing between the pump piston and the pump body bore sidewalls.

It is a feature of this invention that a sampling pump uses the same filter to clean both the fluid entering the pumping chamber and the fluid passing to the operator unit for driving the pump. This filter may be quickly and easily replaced through a side port in the pump body, thereby reducing pump maintenance.

It is another feature of this invention that the pump body includes a purge line for interconnecting the fluid inlet with the fluid outlet and bypassing the pumping chamber, with the purge line being controlled by a valve having its closure member and seat within the pump body.

It is a feature of the invention that a regulator for reducing line pressure to the pump actuator is structurally connected directly to the pump body, and that the output from the regulator may be selectively positioned for hard piping the; regulator to the actuator.

Still another feature of this invention relates to the ease whereby moisture in the regulator may be discharged to increase the reliability of the regulator and the downstream pump actuator.

An advantage of this invention is that the same sampling pump has a diverse number of applications, thereby reducing the overall cost of the pump. The pump of this invention is particularly well suited for withdrawing hydrocarbons from a gathering line connected to a hydrocarbon well, and for discharging the hydrocarbons to a sample container.

A significant advantage of the invention relates to the long life of the seal between the pump piston and the bore sidewalls, particularly when pumping a fluid which tends to deteriorate conventional O-ring seals.

Another advantage of this invention is that water may be automatically discharged from the regulator to a pressurized water container, so that service of the fluid sampling pump is not required to remove accumulated water from the regulator.

These and further objects, features, and advantages of the present invention will become apparent from the following detailed description, wherein reference is made to the figures in the accompanying drawings.

DETAILED DESCRIPTION OF PREFERRED EMBODIMENTS

Figure 1:
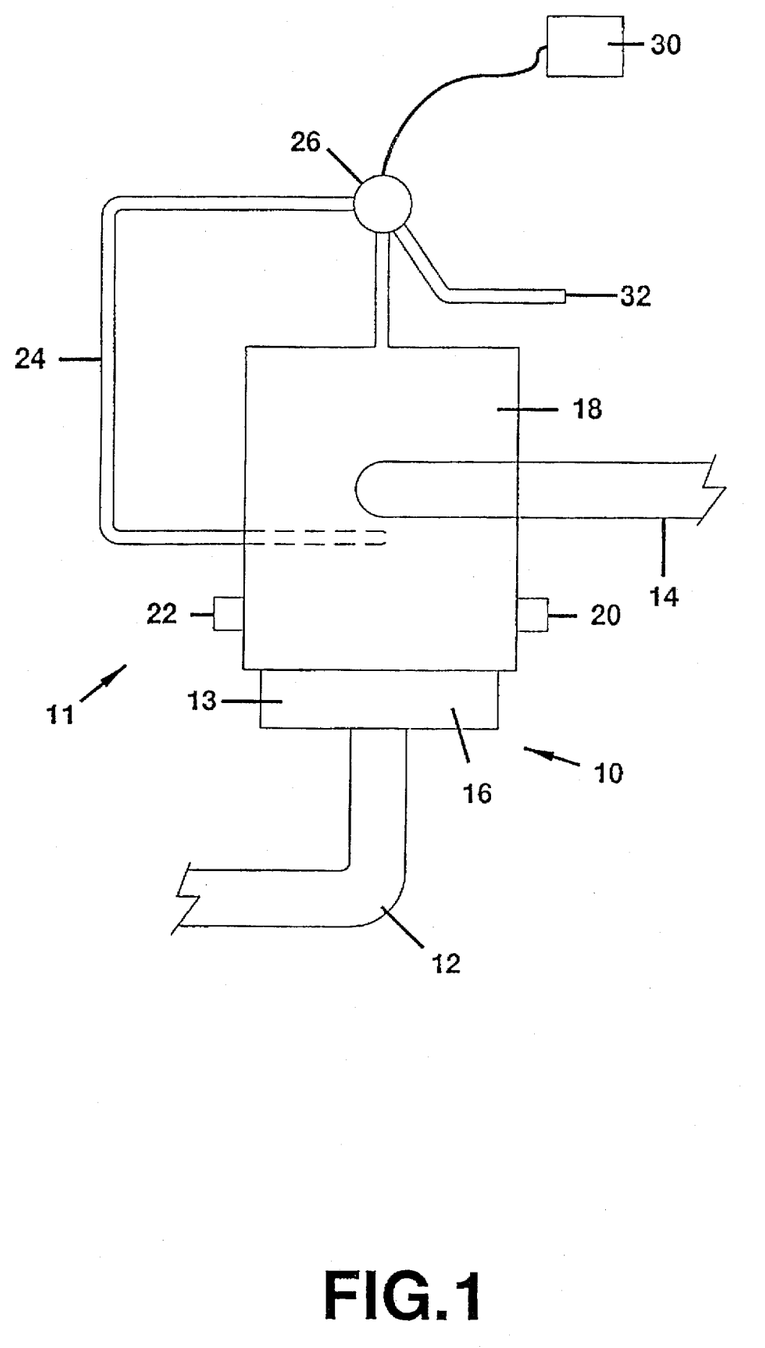
FIG. 1 is a simplistic view of the pump according to the present invention for receiving contaminated fluid from a pressurized source, and for outputting cleaned fluid to a sampling container.

FIG. 1 is a simplistic representation of a pumping assembly 11 according to the present invention for receiving a pressured contaminated fluid from the flow line, container, or other source 12, and outputting a cleaned high pressure fluid to a sampling container, with the sampled fluid passing to the container through output line 14. In an exemplary application, the assembly of the present invention may be used for sampling hydrocarbon gas from various hydrocarbon gathering wells, with the gas being contaminated with scale, debris, or other particulate, and for collecting the sampled hydrocarbon gas in a sampling container. For exemplary purposes, a line 12 may be at approximately 500 psi, while the line 14 and the sampling container may have a final pressure (just prior to removing the sampling container from the pump for testing) of 2500 psi. Also, it should be understood that pump assembly 10 of the present invention may be used with any number of different flow lines or sources depending on the application, and accordingly in another situation line 12 may be a liquid flow line. Also, the output from the pump assembly 10 output line 14 may pass the pumped fluid to a sample bottle or other types of storage vessel.

Still referring to FIG. 1, the overall pumping assembly 11 comprises a pump 10 having a body 13 including inlet housing 16 and pump actuator housing 18. The pump output check valve 20 is simplistically shown for controlling the output pressure to line 14, and a purge valve 22 is also simplistically shown for selectively interconnecting the low pressure line 12 with the output line 14, and thereby purging the pump assembly in a conventional manner. FIG. 1 also shows a solenoid valve 26 in the line 24 for controlling fluid flow to the actuator or operator unit 18. Solenoid valve 26 may be activated by control 30, which may be in the form of an adjustable timer which intermittently sends an activation signal to valve 26 to briefly open the valve and thereby cause a pump driving stroke. The pressure from line 12 is thus used as the power source to drive an actuator unit 18 and thus the pump assembly 10 during the compression stroke of the pump. During the expansion stroke of the pump, fluid within the actuator unit 18 is prevented by valve 26 from flowing back to the pump inlet housing 16 through line 24, and instead is vented to atmosphere or is piped to a safe vent location through exhaust line 32.

Figure 2:
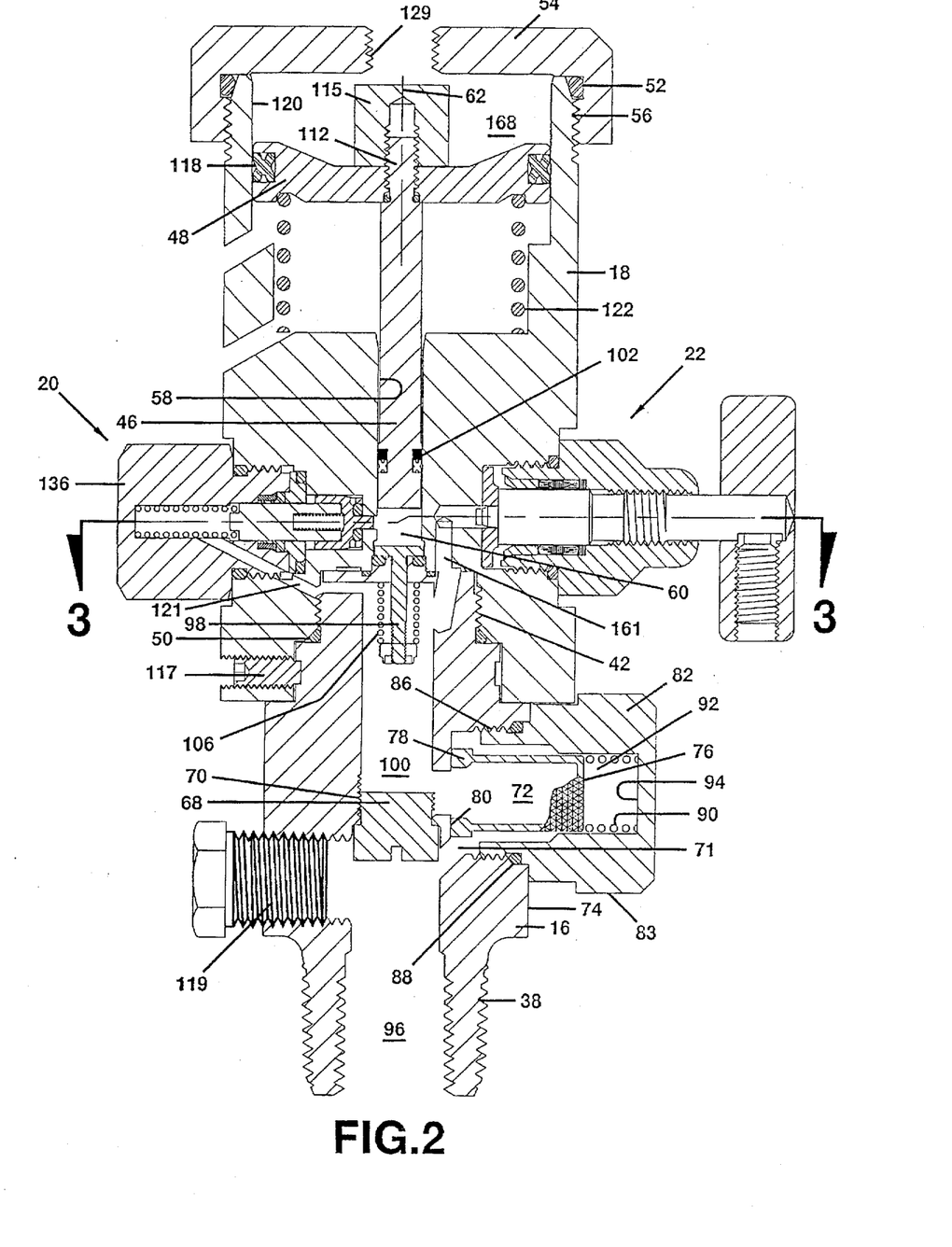
FIG. 2 is a vertical cross-sectional view of a sampling pump according to the present invention.

FIG. 2 depicts in greater detail the pump inlet housing 16 and the actuator housing 18 generally shown in FIG. 1. The pump inlet housing 16 has tapered threads 38 at the lower end thereof for sealing engagement with corresponding threads at the end of line 12. Alternatively, the threads 38 may connected to the upper end of a probe body, which in turn is then connected at its lower end to a line 12. The lower housing 16 is threaded at 42 to an actuator housing 18, which serves as the housing for both the pump plunger or piston 46 and the operator piston 48. A conventional static O-ring seal 50 provides a fluid-tight seal between the mated housings 16 and 18. A similar seal 52 is provided between the upper end of the housing 18 and the actuator cap 54 threaded to the housing at 56. Outlet check valve 20 generally shown in FIG. 1 is depicted in FIG. 2, but is shown in greater detail in FIG. 4 discussed below.

The cylindrical plunger or pump piston 46 is continually in sealed engagement with bore sidewalls 58, so that a pumping chamber 60 is formed within the housing 18, with this chamber having a volume determined as a function of the position of the plunger 46 with respect to the housing 18. Plunger 46 is reciprocated by the actuator unit along axis 62, and moves toward actuator cover 54 during its expansion stroke to draw fluid into the chamber 60 from the line 12, and toward the housing 18 during its compression stroke to expel fluid under high pressure to line 14. The chamber 60 formed by bore sidewalls 58 within the housing 18 has its axis substantially aligned with the axis 62, and serves to receive fluid from the line 12. A diverter member 68 is threaded at 70 to the housing 16, and is positioned along the axis 62 to cause fluid to divert through the connecting passageway 71 to the side port 72 which is formed in the wall of the housing 16 and extends to an outer surface 74 of the housing. A cup-shaped filter 76 is positioned within the port 72, with the circular filter end 78 engaging the planar surface 80 formed by the housing 16. The filter 76 is held in place by filter cap 82, which may be provided with a hexagonal outer surface 83 for threadably connecting and disconnecting the threads 86 between the filter cap and the housing 16. A static O-ring 88 forms a fluid-tight seal between filter cap 82 and the housing 16. A spring or other biasing member 90 is provided within the pocket 92 within the filter cap 82. The pocket 92 has a base surface 94 intentionally spaced a selected distance from the housing 16 to allow the spring 90 to bias filter 76 in the depicted position. As shown in FIG. 2, the combination of the diverter 68 and the filter cap 82 thus causes all fluid which enters pump body through inlet 96 to first pass through the walls of the filter 76 before entering the chamber 100, so that scale, particles, and other debris can be removed by the filter 76. It should also be understood that the filter 76 may be removed, cleaned, and then replaced by unthreading the cap 82, removing the filter 76 from the side port 72 in the housing 16, then reversing the operation to re-install the filter and the cap.

An inlet check valve assembly 98 controls flow of fluid from the chamber 100 downstream of the filter 76 to the pumping chamber 60, and more particularly prevents flow of fluid from the chamber 60 back to the chamber 100 during the pump compression stroke. The inlet check valve assembly includes a valve member which is biased into sealed engagement with an O-ring seal by a spring, so that the seal forms a seal between the head of the valve member and the housing 16 during the compression stroke of the pump. During the pump expansion stroke, the head of the valve member moves upward toward the operator piston 48, thereby compressing the spring 106 positioned about valve member. The lower end of the spring may be supported by nut. If desired, the position of the nut relative to the head of the valve member may be adjusted to change the biasing force of the spring 106, and thereby change the required pressure in the chamber 100 which must be obtained before the check valve assembly 98 opens to allow fluid to pass into the pumping chamber 60.

Spacer 115 is used to control the stoke of the pump. A threaded stud 112 provided at the upper end of the plunger 46 provides sealed engagement with the piston 48, and this sealing may be obtained by using an appropriate pipe dope or another sealing material, such as an O-ring. Seal 118 provides dynamic sealing engagement between the cylindrical wall 120 of the housing 18 and the piston 48, and spring 122 biases the piston 48 upward. The actuator unit cover 54 includes a threaded port 129 for mated engagement with solenoid valve 26 at the end of line 24, as shown in FIG. 1. The plunger 46 is sealed by an improved sealing ring 102 discussed subsequently for sealing engagement with the side walls 58 of the bore or pumping chamber 60. Set screw 117 locks the housing 18 to the housing 16, and pipe plug 119 may be removed for providing a "hot loop" to maintain continuous fluid circulation through inlet 96.

Figure 3:
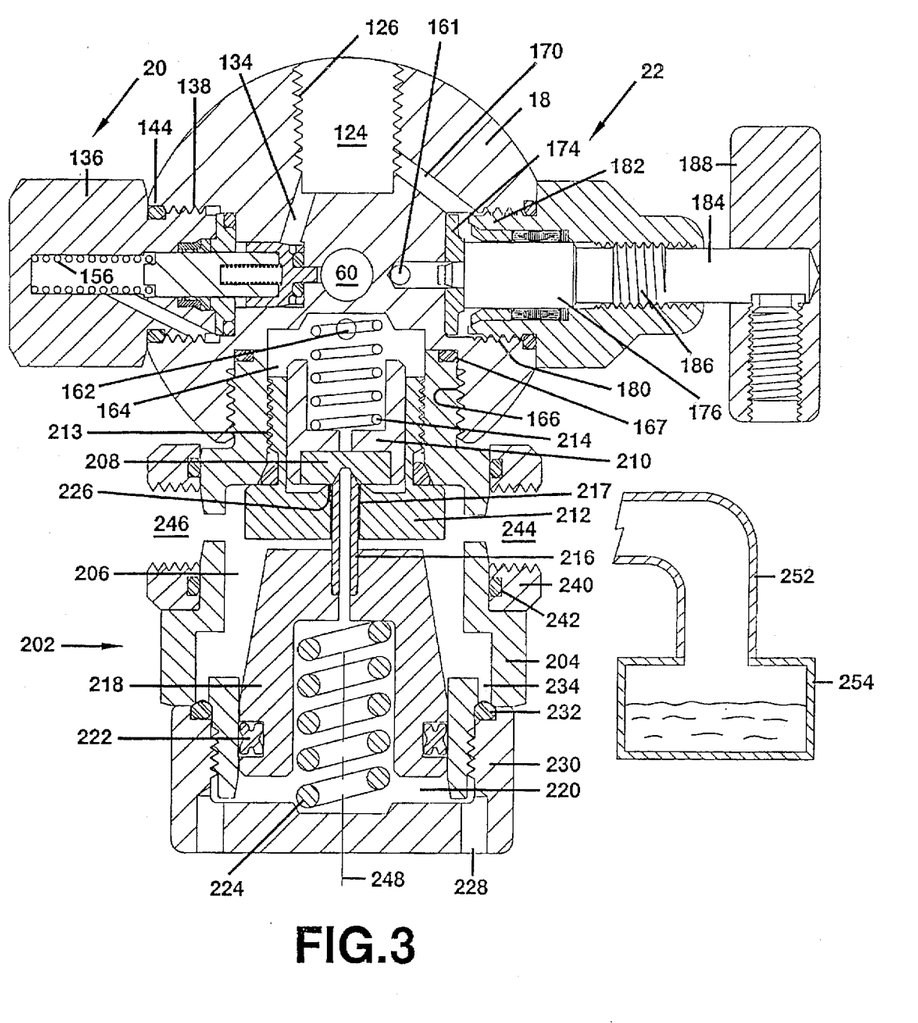
FIG. 3 is a cross-sectional view along line 3—3 of the pump shown in FIG. 2.

FIG. 3 is a cross-sectional view taken along lines 3—3 of FIG. 2. Outlet port 124 includes tapered threads 126 for mated engagement with corresponding threads at the pump end of the line 14. During the compression stroke of the plunger 46, the high pressure fluid seats the check valve assembly 98, so that pressurized fluid flows via passage 134 to the pump outlet port 124, and then through the outlet line 14. Although discussed in greater detail below, it may be seen in FIG. 3 that the outlet cheek valve assembly 20 comprises a housing 136, which may be threaded at 138 for engagement with mating threads provided in a side port in the housing 18, with this side port extending into fluid communication with the compression chamber 60. A static seal 144 provides fluid-tight sealing engagement between the resealable housing 136 and housing 18. The passageway 121 as shown in FIG. 2 provides fluid communication between the chamber 100 and the interior of the housing 136.

Still referring to FIG. 3, the passageway 162 in the body 18 provides fluid communication between the actuator line inlet 164 shown in FIG. 3 and the chamber 100 upstream from the inlet cheek valve assembly 98, as shown in FIG. 2. Filtered fluid may thus pass through passageway 162 to the inlet 164, which includes threads 166 for engagement with the pressure regulator 202 shown in FIG. 3. The regulator body 204 seals with the actuator housing 18 at O-ring seal 167. Cleaned fluid is thus available for passing from the regulator 202 through the line 24 to the port 121 in the cover 54 to fill the chamber 168 above the piston 48, and force the piston and thus the plunger 46 downward during the pump compression stroke. Those skilled in the art will understand that substantially higher pump output pressure compared to operator inlet pressure is obtained due to the substantially large cross-sectional sealing area of the piston 48 compared to the substantially small cross-sectional sealing area of the plunger 46.

FIG. 3 also depicts passageway 170 which provides fluid communication between the fluid output port 124 and the passageway 161, and thus between the output port 124 and the chamber 100, as shown in FIG. 2. The passageway 170 is normally blocked; however, by a closed purge valve assembly 22 which includes an elastomeric seat 174 for sealing engagement between the housing 18 and the valve member 176 of the purge valve 22. Purge valve 22 is fitted within a side port in the housing 18, with mating threads 180 between the body 182 and the housing 18 providing a desired mechanical connection, and an O-ring seal providing a fluid-tight connection between the valve member 176 and both the housing 18 and the sleeve or valve body 182. The valve stem 184 has threads 186 for engagement with mating threads on the body 182, and accordingly rotation of handle 188 will open or closed, the valve member 176 in a conventional manner. During normal use of the pump, the valve 22 remains closed, and fluid is supplied to the actuator unit 18 via the passageway 162 in the body 18 and then via the line 24. The solenoid valve 26 as shown in FIG. 1 is periodically opened to pass fluid from the line 24, and then to the chamber 168 (see FIG. 2) to reciprocate the pump plunger. In order to purge the pump, valve 22 may be opened, so that fluid may flow directly from the pump body inlet port 96 through the filter 76, to the chamber 100 and then to the outlet port 124.

FIGS. 2 and 3 also depict a significant feature of the pump according to the present invention which concerns the positioning of the valves and ports within the pump body or housing. With reference to FIG. 3, the purge valve 22 is mounted on the pump body in a position opposite the cheek valve 20 with respective central axis 62 of the plunger and thus the pump itself. The pump body outlet port is positioned circumferentially between the purge valve 22 and the check valve 20, as shown in FIG. 3. The actuator line port for receiving the regulator 202 is also positioned circumferentially between the purge valve and the check valve, but is opposite the pump body outlet port with respect to the pump centerline. Thus the valves 20 and 22 are preferably generally opposite each other, and ideally 180° opposite each other, with respect to the centerline of the pump, and a first one of the outlet port or actuator line port is positioned circumferentially between these valves, while the other of these ports is also positioned circumferentially between these valves, but is opposite the first port with respect to the pump centerline. This design results in a compact arrangement that is ideally suited for achieving the purposes of the present invention.

The fluid inlet to the regulator body 204 is positioned within the interior of the pump body 18, and regulator 202 is preferably threaded directly to the pump body, and is structurally supported solely by the pump body. The regulator 202 reduces the high pressure in the chamber 100 and thus the regulator input port 164 to a low pressure in the regulator chamber 206. During normal operation of the regulator, the end of rod 216 remains sealed with the disk 208 carried by the dart member. The dart member 210 has a hexagonal outer configuration, so that movement of the dart member is guided by the nut 212 threadably connected to the body 204 at 213, although fluid freely passes between the dart member and the nut to balance the pressure across the dart member. Fluid under line pressure will continually be present in chamber 164, and annular passageway 217 between the exterior cylindrical surface of rod 216 and the interior cylindrical surface of nut 212 provides fluid communication between chamber 164 and the output port 246. The regulator valve mechanism includes disk 208, which acts as a valve to seal with seat 226, which in turn is a functionally stationary part of the nut 212. The disk 208 and dart 210 are forced into sealing engagement with the annular seat 226 by the relatively small biasing force of the spring 214.

Axial movement of the rod 216 thus controls the seating and unseating of seat 208 with the annular lip 226 on the nut 212 to control fluid flow between the high pressure chamber 164 and the low pressure chamber 206, thereby desirably reducing the pressure output from the regulator. When pressure in the downstream port 246 drops below the selected value, the significant downward force of the spring 224 overcomes the reduced fluid pressure acting to force the piston 218 toward the cap 230 thereby forcing the rod 216 to engage the disk 208. One side of the piston 218 is thus exposed to low pressure fluid, while the other side is open to atmosphere through ports 228 in end cap 230. During operation of the regulator, the force of the spring 224 thus biases the rod 226 into engagement with the seat 208 thereby causing the seat 208 to break its seal with lip 226 and allow fluid to pass to chamber 206. If the seal created by lip 226 and disk 208 were to leak, the increased pressure in chamber 206 would cause the rod 216 to unseat from disk 208, thereby venting low pressure from the regulator through ports 228. This operation of the regulator is thus similar to the operation of the regulator disclosed in U.S. Pat. No. 5,090,438.

The regulator of the present invention includes a collar 240 which is rotatable with respect to body 204 while maintaining sealed engagement therewith by normal static O-ring seals 242. One or more ports 244, 246 are provided about circumference of the collar. When the body 204 is threadably connected to the pump body 18 to form the necessary fluid seal and structural interconnection, the orientation of the body 204 about axis 248 is not predictable within reasonable limits. Accordingly, rotation of collar 240 allows for a hard piping connection between regulator (e.g., port 246 in the collar 240 of the regulator) and the pump operator with preformed lengths and bends in the piping or conduit. The spacing along axis 62 (see FIG. 2) and along axis 248 (See FIG. 3) between the threaded port 121 in the cover of 54 and the threaded port 246 in the regulator 202 is thus fixed for a given conduit 24, which may thus be substantially inflexible.

During assembly of the system, the regulator body may be connected to the pump body, then the collar 240 rotated to a selected position for receiving the hard piping connection between the regulator and the pump operator. The structural integrity of the hard piping, once connected between the ports 246 and 121, may thus fix the position of the collar 240 with respect to the regulator body. Alternatively, a set screw or similar securing device (not shown) may be used to structurally fix the position of the collar 240 with respect to the regulator body 204 once the hard piping connection is made.

A significant feature of the invention relates to the capability to easily remove fluids, such as water, from the interior of the regulator 202. Since the fluid being sampled may contain water vapor, condensation may occur within the low pressure chamber 206 due to vapor flashing. This condensation may adversely affect the reliable operation of the regulator, and if the condensation is passed to the pump operator 18, may also affect the performance of the pump operator. The equipment as shown in FIG. 1 is typically installed in an outdoor environment, and accordingly accumulated water within the regulator may freeze, thereby preventing normal operation of the regulator. The assembly as shown in FIG. 1 is periodically serviced, and during such service the operator may unthread but not disconnect, e.g., unscrew one-half turn, the end cap 230 from the body 204, so that accumulated water within the chamber 206 is blown out of the regulator. During this operation, water is passed through the bleed holes 234 and the broken seal 232 due to the increased pressure the chamber 206 compared to atmospheric pressure. This slight unthreading of the end cap does not adversely affect the performance of the regulator, and in fact the end cap 230 can be completely removed and the spring 224, the seal 222, and/or the rod 216 replaced while the pump remains in service. Preferably a plurality of ports or holes 228 are provided about the circumference of the end cap, so that at least one, of the holes 228 will be positioned downward for continually draining wind-driven water or condensate from the atmospheric chamber 220 while the regulator is in use.

The regulator of the present invention is also able to continually discharge fluids from the interior of the regulator without operator service. In this case, a threaded port such as port 244 in the collar 240 is positioned downward for effectively draining condensation from the interior 206 of the regulator. The flow line represented by 252 may be connected in its upper end to the drainage port 244, and at its lower end to a pressurized fluid container 254. Pressure in the fluid container 254 will thus be the same as the pressure in the chamber 206, and condensate will automatically flow from the regulator to the chamber 254. The capacity of the sealed container 254, the fluid being sampled, and the atmospheric conditions surrounding the pump and regulator will thus determine how frequently the container 254 must be emptied.

Figure 4:
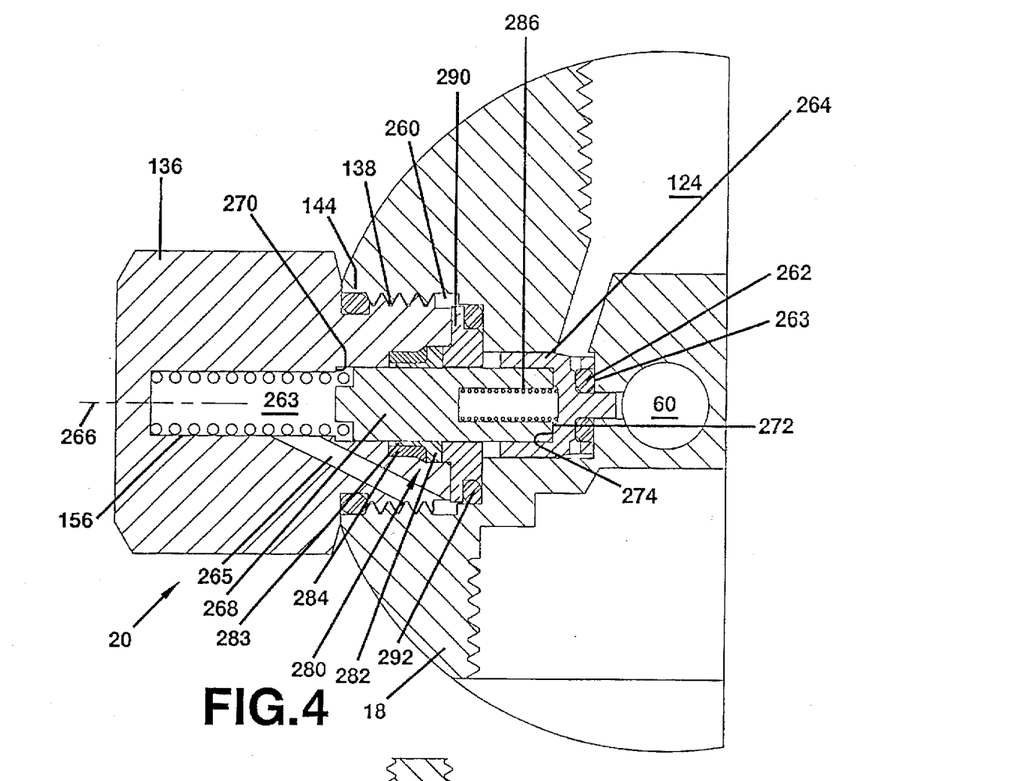
FIG. 4 is a cross-sectional view of a portion of the pump shown in FIG. 2, illustrating particularly the components of the balanced cheek valve.

FIG. 4 depicts in greater detail the balanced check valve 20 for desirably controlling the flow of fluid through the line 14 and to the sample bottle. Line pressure from below the pump inlet check valve assembly 98 (see FIG. 2) continually exists in the passageway 121 and thus the annular chamber 260, the passageway 265 in the housing 136, and the sealed chamber 263 in the housing 136. The seal 280 provides for dynamic sealing engagement between the check valve piston 268 and housing 136, and includes a sleeve shaped member 282 having a substantially L cross-sectional configuration and preferably fabricated from polytetrafluoroethlene, and an elastomeric member formed by a conventional O-ring 284. As may be seen in FIG. 4, only the polytetrafluoroethlene member preferably comes into dynamic sealing engagement with the movable piston 268, and the O-ring member 284 provides a static seal between the housing 136 and the dynamic seal 282, and serves to bias the flexible leg portion 283 of the sleeve member 282 into sealing engagement with the piston 268. A popper spring 286 is substantially housed within the piston 268, and biases the poppet 264 away from the piston 268. Compressor ring 290 guides movement of the piston 268, and a static seal between the body and compressor ring 290 is provided by O-ring 292. As shown in FIG. 4, the compressor ring 290 engages the housing 18 and acts as a stop for engaging the member 282 and thereby compressing the O-ring 284 to make-up the seal 280 as the housing 136 is threadably connected to the housing 18.

During assembly of the seal 280, the sleeve portion 282 of the seal may be placed about the piston 268 and against the ting 290, and an O-ring having a cross-sectional diameter equal to or slightly greater than the maximum thickness of the sleeve portion 282 of the seal may then be placed on top of the sleeve portion 282. The housing 136 may then be threaded to the pump body 18 to sandwich the O-ring 284 between the dynamic seal and the housing 136, thereby compressing and deforming the O-ting seal to the configuration as shown in FIG. 4, so that the O-ring seal 284 effectively serves as a static seal between the housing 136 and the dynamic seal 282, and also serves to bias the leg portion 283 of the dynamic seal into continual sealing engagement with the piston 268. Even if fluids contact the O-ring member 284, the reliable operation of the seal is not adversely affected since the member 284 is not required for dynamic sealing. An O-ring member 284 which is adversely affected by chemicals pumped to the sample bottle to the point that the O-ring member could not maintain a reliable dynamic seal nevertheless will normally retain sufficient elasticity and thus a sufficient biasing force to maintain the member 282 into a reliable dynamic sealing engagement with the piston, and may also maintain a reliable static seal between member 282 and the housing 136 as discussed above.

If line pressure is less than the pressure required to pass fluid to the pump outlet, e.g., line pressure is 500 psi and the check valve 20 is fixed by design to pass fluid at about 600 psi, then the significant increase in pressure during the downstroke of the pump piston 46 will cause the O-ring 262 and the poppet member 264 to move along axis 266 away from seat 263, thereby passing fluid from the chamber 60 to the outlet port 124. The pressure in chamber 124 acts on the radially inward end of the piston 268. If this bottle pressure is greater than the line pressure within chamber 263, the piston will remain in engagement with the stop surface 270, so that end face 272 of the piston 268 is not in engagement with the face 274 of the poppet 264. At this time, the spring 156 is compressed by this pressure differential across the piston 268. During this operation, the check valve assembly 20 as depicted in FIG. 4 thus behaves substantially in the manner of the check valve assembly disclosed in the parent application Ser. No. 08/033,567.

After a new sample bottle is added to a system as shown in FIG. 1, the line pressure typically will be greater than the pressure in the sample container, e.g., line pressure may be 500 psi and the bottle pressure may be 150 psi. In this case, the "balancing" of the check valve assembly is important so that, even before the downstroke of the pump piston, line pressure does not open the check valve assembly and fill the sample bottle with pressure at 500 psi. Line pressure in the chamber 263 acting on the top of the piston 268 thus forces the piston 268 into engagement with the popper 264, so that the faces 272 and 274 are in engagement as shown in FIG. 4. In this case, the pressure in the chamber 60 must rise to the level which will move both the popper 264 and the piston 268 radially outward, thereby compressing the spring 156 and unseating the O-ring 262 to pass fluid to the outlet port 124. Because of the effective cross-sectional differential between the seal 280 and the seal 262, the pressure in the chamber 60 thus must rise to a level higher than the line pressure before the poppet 264 and the piston 268 are axially moved to release pressure to the chamber 124. The same balancing of a check valve assembly also prevents the sample container from unintentionally filling with fluid from the pressurized line in the event that line pressure was expected to be 500 psi, but the line pressure then unexpectedly increased to 700 psi. By operation of a conventional check valve set at 600 psi, line pressure would pass directly to the bottle and fill the bottle at 700 psi. According to the present invention, however, this increase in line pressure acts on the top of the piston 268, so that the check valve is balanced and a fluctuation in line pressure will not undesirably effect the operation of the pump.

Figure 5:
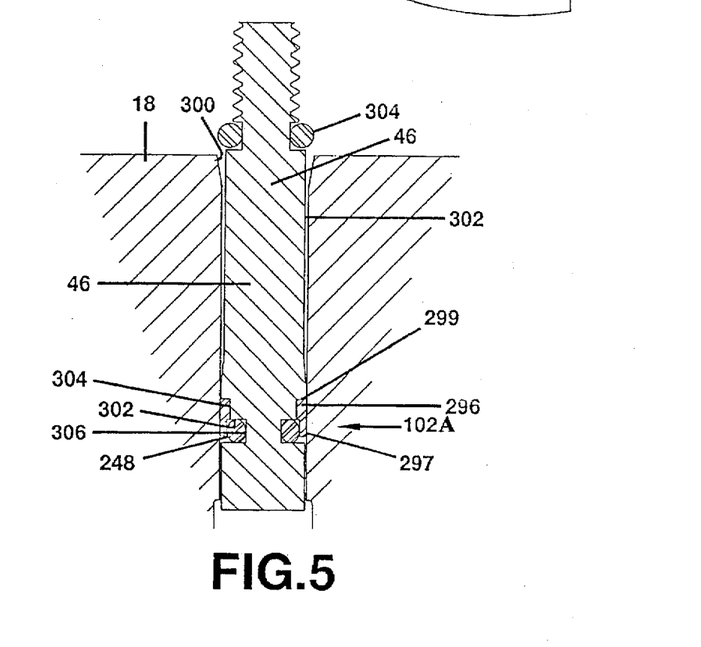
FIG. 5 is a cross-sectional view of a portion of the pump shown in FIG. 2, including particularly the piston within the bore of the pump body and the seal components for dynamic sealing between the piston and the pump body bore sidewalls.

Referring to FIG. 5, an O-ring 304 may be provided on the piston 46 for sealing engagement between the piston 46 and the operator piston 48. FIG. 5 shows further details with respect to the improved seal 102A according to the present invention for dynamic sealing engagement between the pump piston 46 and the housing 18. The seal 102A according the present invention consists of a polytetrafluoroethlene member 296 which in cross-section has inverted L-shaped configuration and an O-ring member 298 which may be formed from a conventional elastomeric material. As with the seal 280 discussed above, the seal 102 includes a low friction, long life, and chemically inert member 296 which provides the dynamic seal between the movable member, i.e., the piston 46, and the body 18. The O-ring 298 provides a static seal between the piston 46 and the member 296, and also provides the radial outward biasing force to maintain the leg 297 of the dynamic member 296 in continual sealing engagement with the body 18. The seal 102A as shown in FIG. 5 is particularly well suited when pumping a fluid which would be corrosive or otherwise deleterious to conventional sealing materials. Certain features of the seal 102A, including those relating to long seal life, are thus similar to the seal disclosed in U.S. Pat. No. 4,597,581.

A feature of the invention relates to the technique which forms low cost and highly reliable seal between the pump body and the plunger, thereby providing long life for the pump and thus for the assembly as shown in FIG. 2. During assembly of seal 102A, both the seal members 296 and 298 may be placed on the plunger or piston 46, with the lower deflectable end 297 of the member 296 being biased outwardly due to the O-ring 298. This outward deflection of the lower end 297 will nevertheless allow the seal assembly to fit within the chamfered area 300 of the actuator body 18. A thin annulus 302 may be provided between a reduced diameter portion of the piston and the sidewalls of the body to reduce manufacturing costs. This reduced diameter portion thus has a diameter only slightly less than the full diameter of the piston in the vicinity of the seal 102A.

To form the seal of the present invention, the chamfered surface 300 is thus formed at the pump body at the end of the bore for receiving the piston. An annular groove 302 is formed about the piston 46 as noted above. The piston 46 includes a dynamic seal receiving portion 304 and an adjoining elastomeric receiving portion 306 having a radial cross-section greater than portion 304. The elastomeric sealing member 298 preferably is an O-ring which may be formed from a selected elastomeric material, and the dynamic sealing member 296 is a plastic material member, and preferably polytetrafluoroethlene. The dynamic sealing member 296 preferably has an upper body portion 299, and radially thinner and deflectable portion 297 which, as explained above, is normally biased outwardly by the elastomeric sealing member 298. The body portion 299 of the dynamic seal thus serves to properly position the leg member 297 with respect to the elastomeric seal 298. The elastomeric seal 298 does not exert a significant radially outward force on the body portion 296, and instead primarily acts on the radially thinner portion 297 to form the desired dynamic seal.

Various modifications to the pump will be apparent from the foregoing description, and the pump of the present invention may be designed for utilization with various upstream fluids maintained at different pressure ranges. The pump of the present invention may be used for applications wherein the pump is not withdrawing a sampling fluid from a line, tank, or other source, then outputting fluid to a container. In such another application, the pump may withdraw a small volume of fluid from a source, such as a pressure bottle housing a highly olfactic gas, and discharging that olfactic gas to a natural gas distribution line. In this application, the pump is thus acting as an injection pump to inject a small amount of olfactic gas in the natural gas line to assist in gas leakage detection. Accordingly, it should be understood that the upstream source for supplying fluid to the pump of the present invention should be construed to mean any upstream line, tank, or other chamber housing the upstream fluid, and the term "container" or "sample bottle" that receives the output fluid from the pump should similarly be understood to include not only conventional sampling container, but also a downstream line or another chamber that receives the downstream fluid.

According to the method of the present invention, the upstream contaminated fluid is filtered by a filter positioned within the pump body, and the same filter cleans fluids entering the pumping chamber and fluids supplied to the actuator unit to drive the pump. The filter may be easily checked and cleaned, if necessary, by unthreading a resealable plug provided in the pump body side port, removing the filter, then re-installing the cleaned filter and plug. Fluid within the pump body may be diverted by a member positioned along the plunger axis between the plunger and the pump body inlet. The fluid pump may be purged by the service technician, if desired, by operating a purge valve that has its seat also within the pump body. To adjust the stroke of the piston, the actuator cap 54 may be removed from the pump actuator body, and the spacer 115 replaced with a new spacer. Various alternative methods of operating a pump will be apparent to those skilled in the art from the above description. Further details with respect to the pump and the method of the present invention are disclosed in pending application Ser. No. 08/033,567 filed Mar. 18, 1993.

Additional modifications and alterations to the embodiments and methods described above should now be apparent to one skilled in the art from the foregoing description. Various further modifications may thus be made in accordance with the teachings of the present invention, and the invention is thus not restricted to the preferred embodiments discussed herein and shown in the accompanying drawings. The scope of the invention should thus be understood to include all embodiments within the reasonable scope of the following claims.

What is claimed is:

1. A method of forming a seal between a pump body and a pump plunger reciprocatingly movable within a bore of the pump body for varying the volume of a fluid receiving chamber within the pump body to receive fluid from a source and discharge fluid to a container during a pumping cycle, the method comprising:

forming a chamfered surface on the pump body at the end of the bore;

forming an annular groove about the plunger, the annular groove having the dynamic seal receiving portion and an adjoining elastomeric seal receiving portion;

positioning an elastomeric sealing member within the elastomeric seal receiving-portion;

positioning a dynamic sealing member within the dynamic seal receiving portion such that at least a portion of the dynamic sealing member is biased radially outward by the elastomeric sealing member; and inserting the plunger, the elastomeric sealing member, the dynamic sealing member including a body portion and deflectable leg portion radially thinner than the body portion and axially spaced from the body portion and the dynamic sealing member into the bore such that the radially biased portion of the dynamic sealing member engages the chamfered surface to forceably move the portion of the dynamic sealing member radially inward, thereby compressing and deforming the elastomeric sealing member such that the elastomeric sealing member forms a static seal between the plunger and the dynamic sealing member and biases the portion of the dynamic sealing member into dynamic sealing engagement with the pump body.

2. The method as defined in claim 1, further comprising:

forming the dynamic sealing member such that it has a body portion and a deflectable leg portion extending axially from the body portion, such that the leg portion of the dynamic sealing member is biased radially outward by the elastomeric sealing member.

3. The method as defined in claim 1, wherein the elastomeric sealing member is an O-ring member formed from a selected elastomeric material, and the dynamic sealing member is a plastic material member.

4. The method as defined in claim 3, wherein the dynamic sealing member is formed from polytetraflourethylene.

5. The method as defined in claim 1, further comprising:

forming a reduced diameter portion on the plunger having a diameter less than a full diameter of the plunger adjacent the seal, such as an annulus is formed between the reduced diameter portion and the pump body.

6. A sampling pump for withdrawing fluid from a pressurized source and outputting fluid to a container, the pump comprising:

a pump body having a pump body inlet for fluid-tight communication with the pressurized source, a pump body outlet for fluid-tight communication with the container, and a fluid receiving chamber;

a plunger axially reciprocal within the fluid receiving chamber in the pump body for varying the volume of the fluid receiving chamber within the pump body to receive fluid from the pressurized source and discharge fluid to the container during a complete pumping cycle, the plunger having an annular groove therein, the groove having a dynamic seal receiving portion and an adjoining biasing seal receiving portion;

a pump inlet check valve for preventing fluid flow from the fluid receiving chamber to the pump body inlet;

a discharge check valve for preventing fluid flow from the container to the fluid receiving chamber; and a seal within the annular groove in the plunger for dynamic sealing between the plunger and the pump body, the seal having a dynamic sealing member positioned within the dynamic seal receiving portion and including a body portion and deflectable leg portion radially thinner than the body portion and axially spaced from the body portion, and a biasing sealing member within the biasing seal receiving portion, such that the leg portion of the dynamic sealing member is biased radially outward by the biasing sealing member is biased radially outward by the biasing sealing member into sealing engagement with the pump body and the biasing sealing member forming a static seal between the plunger and the dynamic sealing member and biasing the leg portion of the dynamic sealing member into dynamic sealing engagement with the pump body.

7. The sampling pump as defined in claim 6, wherein the biasing sealing member is an O-ring member formed from a selected elastomeric material, and the dynamic sealing member is a plastic material member.

8. The sampling pump as defined in claim 7, wherein the dynamic sealing member is formed from polytetrafluoroethylene.

9. The sampling pump as defined in claim 7, further comprising:

the plunger having a reduced diameter portion with a diameter less than a full diameter of the plunger adjacent the seal, such that an annulus is formed between the reduced diameter portion and the pump body.

10. The sampling pump as defined in claim 6, further comprising:

a filter for filtering fluids passing from the fluid inlet to the fluid receiving chamber;

the pump body fluid inlet having an inlet axis substantially aligned with an axis of the plunger; and a diverter member positioned along the plunger axis and between the plunger and the pump body fluid inlet for diverting fluid flow through the filter.

11. The sampling pump as defined in claim 10, further comprising:

an operator unit powered by fluid pressure for reciprocating the plunger; and a fluid pressurizing line having an inlet positioned between the filter and the pump inlet check valve and an outlet in fluid communication with the operator unit.

12. The sampling pump as defined in claim 6, further comprising:

a purge line interconnecting the pump body inlet and the pump body outlet; and a purge valve positioned along the purge line and having a valve member movable within the pump body for selectively controlling fluid flow from the pump body inlet to the pump body outlet.

13. A pump for pumping fluid, the pump comprising:

a pump body having a pump body inlet, a pump body outlet, and a fluid receiving chamber;

a plunger axially reciprocal within the fluid receiving chamber in the pump body for varying the volume of the fluid receiving chamber within the pump body to receive fluid from the pump body inlet and discharge fluid through the pump body outlet during a complete pumping cycle, the plunger having an annular groove therein, the groove having a dynamic seal receiving portion and an adjoining biasing seal receiving portion;

a pump inlet check valve for preventing fluid flow from the fluid receiving chamber to the pump body inlet;

a discharge check valve for preventing fluid flow from the pump body outlet to the fluid receiving chamber; and a seal within the annular groove in the plunger for dynamic sealing between the plunger and the pump body, the seal having a dynamic sealing member positioned within the dynamic seal receiving portion and including a body portion and deflectable leg portion radially thinner than the body portion and axially spaced from the body portion, and a biasing sealing member within the biasing seal receiving portion, such that the leg portion of the dynamic sealing member is biased radially outward by the biasing sealing member into sealing engagement with the pump body and the biasing sealing member forming a static seal between the plunger and the dynamic sealing member and biasing the leg portion of the dynamic sealing member into dynamic sealing engagement with the pump body.

14. The pump as defined in claim 13, wherein the biasing sealing member is an O-ring member formed from a selected elastomeric material, and the dynamic sealing member is a plastic material member.

15. The pump as defined in claim 14, wherein the dynamic sealing member is formed from polytetrafluoroethylene.

16. The pump as defined in claim 14, the plunger having a reduced diameter portion with a diameter less than a full diameter of the plunger adjacent the seal, such that an annulus is formed between the reduced diameter portion and the pump body.

17. The pump as defined in claim 13, further comprising:

the pump body fluid inlet having an inlet axis substantially aligned with an axis of the plunger; and a diverter member positioned along the plunger axis and between the plunger and the pump body fluid inlet for diverting fluid flow.

18. The pump as defined in claim 13, further comprising:

a purge line interconnecting the pump body inlet and the pump body outlet; and a purge valve positioned along the purge line and having a valve member movable within the pump body for selectively controlling fluid flow from the pump body inlet to the pump body outlet.

* * * * *